United States Patent [19]

Grollier et al.

[11] Patent Number: 4,839,166
[45] Date of Patent: Jun. 13, 1989

[54] COSMESTIC COMPOSITIONS CONTAINING A CATIONIC POLYMER AND AN ANIONIC POLYMER AS THICKENING AGENT

[75] Inventors: Jean F. Grollier, Paris; Claude Dubief, Le Chesnay; Jean Mondet, Drancy, all of France

[73] Assignee: L'Oreal, Paris, France

[21] Appl. No.: 49,785

[22] Filed: May 15, 1987

[30] Foreign Application Priority Data

May 16, 1986 [LU] Luxembourg ............................ 86 429

[51] Int. Cl.$^4$ .......................... A61K 7/11; A61K 7/48; A61K 7/06; B01J 13/00
[52] U.S. Cl. ......................................... 424/71; 424/78; 424/70; 424/61; 252/315.3; 252/315.4; 526/932
[58] Field of Search ....................... 424/61, 70, 71, 78, 424/DIG. 2; 526/932; 252/315.1, 315.3, 315.4

[56] References Cited

U.S. PATENT DOCUMENTS

| | | | |
|---|---|---|---|
| 3,472,840 | 10/1969 | Stone et al. | 536/31 X |
| 3,579,632 | 5/1971 | Sonnen | 424/70 |
| 3,962,418 | 6/1976 | Birkofer | 424/70 |
| 4,131,576 | 12/1978 | Iovine et al. | 527/313 X |
| 4,240,450 | 12/1980 | Grollier et al. | 132/7 |
| 4,501,834 | 2/1985 | Su | 524/28 |
| 4,591,610 | 5/1986 | Grollier | 524/55 |
| 4,638,222 | 1/1987 | Grollier et al. | 424/70 X |

FOREIGN PATENT DOCUMENTS

| | | |
|---|---|---|
| 2528699 | 12/1983 | France . |
| 2025228 | 1/1980 | United Kingdom ................. 424/70 |
| 2098226 | 11/1982 | United Kingdom . |
| 2098624 | 11/1982 | United Kingdom . |
| 2114580 | 8/1983 | United Kingdom . |
| 2123694 | 2/1984 | United Kingdom . |
| 2134784 | 8/1984 | United Kingdom . |

OTHER PUBLICATIONS

Encyclopedia of Polymer Science and Technology, vol. 1, 1964, pp. 191–192 and 221–222.

*Primary Examiner*—Ellis P. Robinson
*Assistant Examiner*—Susan S. Rucker
*Attorney, Agent, or Firm*—Fleit, Jacobson, Cohn & Price

[57] ABSTRACT

Thickening agent resulting from the interaction of a copolymer of cellulose or of a cellulose derivative which are grafted with a quaternary ammonium salt of a water-soluble monomer and of a carboxylic anionic polymer and cosmetic compositions in which it is present.

15 Claims, No Drawings

COSMESTIC COMPOSITIONS CONTAINING A CATIONIC POLYMER AND AN ANIONIC POLYMER AS THICKENING AGENT

The present invention relates to a new gelling or thickening agent, new thickened or gelled cosmetic compositions containing such an agent and a process enabling such compositions to be gelled and/or thickened.

A general requirement existing in the cosmetics industry is for compositions for hair or for the skin which do not flow too quickly; such is the case, in particular, with the compositions employed in processes which involve periods of application or of contact of the composition with the hair or the skin. It is very advantageous, in this case, to employ compositions which have a viscosity index higher than a certain limit enabling the products to be properly localized with the aid of thickened solutions.

In previous patents such as French Patents 2,383,660, 2,505,179 and 2,542,997, the applicant has already described compositions containing cationic polymers and anionic polymers in an aqueous medium and capable of being presented in the form of thickened or gelled compositions. The polymers are employed in these compositions in order to impart to hair advantageous shape-retention, sheen and disentangling properties. These compositions are optionally thickened with a gelling or thickening agent which is added to the polymers.

Such gelled or thickened compositions of the prior state of the art have the disadvantage, however, resulting from the presence of the gelling or thickening agents, of excessively loading the hair or of leaving an unattractive powdery deposit or, yet again, of imparting to it an unpleasant feel or a dull appearance, particularly when involving compositions whose application is not followed by a rinse.

These compositions, which contain a gelling or thickening agent in addition to the polymers, are sometimes cloudy or opaque, and this can prevent their use in certain applications such as, for example, hair-shaping compositions which are generally clear.

Because of this, the applicant has investigated the possibility of preparing gelled or thickened aqueous cosmetic compositions conferring onto hair the advantageous shape-retention and sheen properties of the compositions containing cationic and anionic polymers, while avoiding the abovementioned disadvantages due to the addition of gelling agents or thickeners.

It has, furthermore, already been recommended to form gels from a polymer derived from a quarternary ammonium of cellulose ether as described in U.S. Pat. No. 3,472,840 and from an anionic polymer chosen from alginic acid or a polysulphonic acid such as 2-acrylamido-2-methylpropanesulphonic acid. The gelled compositions produced in this manner result, on the one hand, from the use of anionic polymers which themselves have thickening or gelling properties and, furthermore, require relatively high solids concentrations. Furthermore, such compositions are not completely satisfactory when they are employed for conditioning hair damaged by physical or chemical treatments or by atmospheric agents.

The applicant has now found that it is possible to prepare aqueous cosmetic compositions which are gelled or thickened merely by the presence in these compositions of a copolymer of cellulose or of a cellulose derivative which are grafted preferably by a radical route with a quaternary ammonium salt of a water-soluble monomer and certain carboxylic anionic polymers. A synergistic effect is obtained which appears to be due, though this is merely a hypothesis, to the formation of an interpolymer by ionic interaction in an aqueous medium. To make the definition easier, the term "thickness" is employed in the remainder of the description to denote the product having thickening and/or gelling properties resulting from this interaction. The thickener obtained in this manner should have an Epprecht-Drage viscosity at 21° C., module 3, measured diluted with water to a concentration of 1%, which is equal to or higher than 0.450 Pa s, while the absolute capillary viscosity of the anionic polymer containing carboxylic groups, measured at 30° C. in solution in dimethylformamide or methanol at a concentration of 5%, is lower than or equal to 0.030 Pa s and while the cationic copolymer has an absolute capillary viscosity at 1% in water at 30° C. which is also lower than 0.025 Pa s. The formation of a thickening agent is particularly surprising insofar as it results from polymers which do not individually have such thickening properties under these conditions of use. This capacity is markedly superior to that of gels known previously, some of which have been produced using anionic polymers which themselves have gelling properties. This is particularly advantageous within the scope of the present invention because the thickening characteristics make it possible not only to achieve a saving in the use of the polymers to obtain an identical gelling but at the same time make it possible to impart to the hair or to the skin which are treated with these compositions certain improved cosmetic properties without loading the hair excessively.

Furthermore, the new cosmetic compositions have the advantage of not loading the hair, even when the applications are repeated, especially in the case of compositions which are applied using methods which do not involve a rinsing stage, and of imparting a pleasant feel and a gleaming appearance to the hair. They impart good shape retention and good liveliness to hair, and more particularly to fine hair, in the case of the compositions whose application is followed by a water rinse. Lastly, these compositions make it possible to improve the treatment of damaged hair, especially insofar as its disentangling, its softness and its feel are concerned.

The subject of the present invention is consequently a thickener resulting from an ionic interaction in an aqueous medium of a copolymer of cellulose or of cellulose derivatives grafted by a radical route with a quaternary ammonium salt of a water-soluble monomer and a particular group of carboxylic anionic polymers and its use for thickening or gelliing cosmetic compositions.

Another object of the invention consists of the cosmetic compositions intended for the treatment of hair or of the skin containing this new thickening agent.

Another subject of the invention is a process for the treatment of hair or of the skin making use of this thickener or the compositions containing it.

Another subject of the invention consists of a process for gelling or increasing the viscosity of a cosmetic composition by making use of the thickener defined above.

Other objects of the invention will become apparent from reading the description and the examples which follow.

The thickening agent according to the present invention is essentially characterized in that it results from the ionic interaction in an aqueous medium between a copolymer of cellulose or of a cellulose derivative which is grafted by a radial route with a quaternary ammonium water-soluble monomer and a carboxylic anionic polymer having an absolute capillary viscosity when diluted to a concentration of 5% in dimethylformamide or methanol and at a temperature of 30° C. which is lower than or equal to 0.030 Pa s, this thickener having an Epprecht-Drage viscosity at 21° C., module 3, measured diluted to a concentration of 1% in water, which is equal to or higher than 0.0450 Pa s.

The cationic polymer employed for the preparation of the thickener is chosen more particularly from polymers of cellulose or of cellulose derivatives consisting of hydroxyalkyl celluloses such as hydroxymethyl cellulose, hydroxyethyl cellulose or hydroxypropyl cellulose which are grafted by a radical route with a quaternary ammonium salt of a water-soluble monomer chosen from methacryloylethyltrimethylammonium, methacrylamidopropyltrimethylammonium and dimethyldiallylammonium salts, and more particularly the halides such as the chlorides, or the methosulphates.

Particularly preferred products consist of the hydroxyethyl cellulose copolymer grafted by a radical route with diallyldimethylammonium chloride sold under the trade name "Celquat L 200" or "Celquat H 100" by National Starch, which are also called "Polyquaternium 4" in the CFTA dictionary. When diluted to a concentration of 1% in water and at a temperature of 30° C., these polymers have an absolute capillary viscosity of the order of 0.01 Pa s in the case of the product marketed under the trade name "Celquat L 200" and 0.021 Pa s in the case of the product marketed under the trade name "Celquat H 100".

The anionic polymers employed in accordance with the invention are carboxylic anionic polymers having a molecular weight of between 500 and 3,000,000 and more particularly between 1,000 and 3,000,000. These are preferably film-forming polymers.

Particularly preferred polymers are chosen from:

(a) methacrylic acid homopolymers which have a molecular weight greater than 20,000, as determined by light scattering, (b) copolymers of methacrylic acid with one of the following monomers:

$C_1$-$C_4$ alkyl acrylate or methacrylate;

an acrylamide derivative such as, more particularly, N,N-dimethylacrylamide, diacetoneacrylamide or N-tert-butylacrylamide;

maleic acid;

$C_1$-$C_4$ monoalkyl maleate; and

N-vinylpyrrolidine, (c) copolymers of ethylene with maleic anhydride, such as the products sold under the trade name EMA 31 by Monsanto Cie.

Particularly preferred anionic polymers are methacrylic acid copolymers which have an absolute capillary viscosity measured at a concentration of 5% in solution in dimethylformamide or methanol, at 30° C., of between 0.003 and 0.030 Pa s, and more particularly the copolymer of methacrylic acid with methyl methacrylate whose absolute capillary viscosity, measured at a concentration of 5% in solution in a dimethylformamide, is of the order of 0.015 Pa s or a copolymer of methacrylic acid with monoethyl maleate which has an absolute capillary viscosity, measured at a concentration of 5% in solution in dimethylformamide, of the order of 0.013 Pa s, a copolymer of methacrylic acid with butyl methacrylate whose absolute capillary viscosity, measured at a concentration of 5% in solution in methanol, is of the order of 0.010 Pa s, or a copolymer of methacrylic acid with maleic acid whose absolute capillary viscosity, measured at a concentration of 5% in solution in dimethylformamide, is of the order of 0.016 Pa s.

The thickener may be prepared under the following conditions:

a quantity of water required to dissolve it is added to the copolymer of cellulose or of cellulose derivatives grafted by a radical route with a quaternary ammonium salt of a water-soluble monomer (solution I).

Separately, a quantity of water required to dissolve it is added to the carboxylic anionic polymer, the dissolution being promoted by neutralization with a conventional alkalifying agent such as aqueous ammonia or the alkanolamines (solution II).

The thickener is then formed by adding solution I to solution II or vice versa, with stirring, at ambient temperature. When the gel has formed it can then, if desired, be diluted with water or with a mixture of water and alcohol, the proportion of alcohol being that required to produce the required alcoholic strength for the formulation.

According to an alternative form of this process, it is equally possible, without recourse to neutralization, to dissolve the carboxylic anionic polymer in alcohol, preferably ethanol, at a concentration such as to bring the final formulation to the alcoholic strength required. The thickener may also be formed in the aqueous cosmetic medium itself.

The copolymer of cellulose or of a cellulose derivative which is grafted by a radical route with a quaternary ammonium is present preferably in the aqueous medium in proportions of between 0.01 and 6% by weight, particularly between 0.1 and 1.5%, based on the weight of the medium; the carboxylic anionic polymer is present in the aqueous medium in a proportion preferably of 0.01 to 6%, particularly from 0.1 et 1.5%, by weight based on the weight of the medium, and the weight ratio of the cationic polymer to the carboxylic anionic polymer is between 1/5 and 5/1; it is preferably between ½ and 2/1 and more particularly equal to about 1.

The thickened or gelled cosmetic compositions intended for the treatment of hair and of the skin, according to the invention, are essentially characterized in that they contain at least one copolymer of cellulose or of a cellulose derivative which is grafted by a radical route with a quaternary ammonium salt of a water-soluble monomer and a carboxylic anionic polymer and in sufficient proportions to form the thickener by ionic interaction, so that a composition containing 1% of this thickener in water has an Epprecht-Drage viscosity at 21° C., module 3, which is equal to or higher than 0.450 Pa s.

The thickener is present in the cosmetic composition according to the invention in concentrations which vary between 0.02 and 12%, preferably between 0.2 and 3%, by weight based on the total weight of the composition.

This composition is presented in aqueous form, but it may contain other cosmetically acceptable solvents such as, for example, lower alcohols such as ethanol or isopropanol, glycerol, glycols or glycol ethers such as ethylene glycol monobutyl ether, propylene glycol, diethylene glycol monoethyl ether and monomethyl ether, and in proportions which do not affect the formation of the thickener.

These compositions have a pH which is generally between 6 and 12 and preferably between 6.5 and 9 and, more particularly, is close to neutrality and is of the order of 7 to 8.

It may be adjusted with an alkalifying or acidifying agent which is usually employed in the field of cosmetics.

The gelled or thickened cosmetic compositions containing a thickener such as defined above may be employed as a shampoo, after-shampoo compositions, products for rinsing to be applied before or after shampooing, before or after dyeing or bleaching, before or after permanent-waving or hair straightening, as a hair-setting or blow-drying composition, as a restructuring composition, or as a support for permanent-waving or for dyeing or bleaching hair. These thickened or gelled compositions may also contain a dermatological active principle such as antidandruff, antiseborrhoeic, antiacne, antifungal, bactericidal, keratolytic or antipsoriatic agents.

When the compositions according to the invention are employed in the form of thickened lotions or gels for hair-setting or for blow-drying, they may optionally contain other polymers which are usually employed in a composition of this type, and more particularly nonionic polymers such as polyvinylpyrrolidones, copolymers of polyvinylpyrrolidone with vinyl acetate, or anionic polymers which do not have the abovementioned properties of gelling or thickening with the cationic polymer. As an example, there may be mentioned copolymers of vinyl acetate with an unsaturated carboxylic acid such as crotonic acid, copolymers resulting from the copolymerization of vinyl acetate with crotonic acid and an acrylic or methacrylic ester, copolymers resulting from the copolymerization of vinyl acetate with an alkyl vinyl ether and an unsaturated carboxylic acid and copolymers resulting from the copolymerization of vinyl acetate with crotonic acid and a vinyl ester of an acid containing a long carbon chain or an allyl or methallyl ester of an acid containing a long carbon chain. These polymers are employed in concentrations of between 0.1 and 5% by weight based on the total weight of the composition.

When employed as rinsing compositions, they may contain various conditioning agents such as quaternary proteins, cationic silicone polymers, cationic surfactants and cationic polymers other than polymers of cellulose or of cellulose derivatives grafted by a radial route with a quaternary ammonium water-soluble monomer, of the polyamine, polyaminoamide or quaternary polyammonium type.

When the compositions are employed as shampoos, they contain surface-active agents with detergent properties which are known per se, such as anionic, cationic, nonionic or amphoteric surface-active agents or mixtures thereof.

In general, these surface-active agents are present in proportions of between 0.1 and 30% by weight based on the total weight of the composition.

When the compositions are employed for dyeing hair, they contain direct dyes or oxidation dye precursors which are well known in the art.

The compositions according to the invention may also be employed as products for conditioning skin and nails.

A particularly preferred cosmetic composition is a hair-shaping composition which is not rinsed off. This composition contains, in aqueous or aqueous-alcoholic solution, a thickener resulting from the ionic interaction of 0.1 to 1.5% by weight of a hydroxyethyl cellulose copolymer grafted by a radical route with diallyldimethylammonium chloride and from 0.1 to 1.5% by weight of a copolymer of methacrylic acid with (a) methyl methacrylate, or
(b) monomethyl maleate, or
(c) butyl methacrylate, whose absolute capillary viscosity, measured at 30° C. at a concentration of 5% in solution in dimethylformamide or methanol, is between 0.010 and 0.015 Pa s, the Epprecht-Drage viscosity of the thickener, measured at 21° C., module 3, diluted to a concentration of 1% in water, being higher than 0.0450 Pa s, the pH of the composition being between 6.5 and 9.

The compositions according to the invention may contain any other ingredient which is usually employed in cosmetics, such as perfumes, colourants, preservatives, sequestering agents, softeners or silicones.

The process for thickening or gelling cosmetic compositions which forms another subject of the invention consists essentially in introducing into a cosmetic composition, in aqueous form, at least one thickener such as defined above or a composition containing the polymers forming the thickener in proportions of 0.02 to 12% by weight based on the total weight of the composition so as to give an Epprecht-Drage viscosity of the composition which is equal to or higher than 0.450 Pa s.

Aqueous gels or thickened compositions containing the thickener may be prepared separately, and the cosmetic composition may be prepared in a different step, if desired at the time of use.

The process for the treatment of hair, of the skin and of the nails consists in applying to them a composition such as defined above, it being possible for this composition to be rinsed off with water, or not, according to the nature of the treatment desired.

The applicant has found that this composition for the treatment of hair not only made it possible to localize the product on hair properly without flowing onto the face but that the hair trated in this manner also had a pleasant feel and a shiny appearance. Furthermore, the thickened or gelled composition has the advantage of being clear.

The examples which follow are intended to illustrate the invention without, however, being limiting in nature.

EXAMPLE 1

Aqueous gels were prepared according to the information which appears in Table 1 which follows. For this purpose, 50 cm$^3$ of an aqueous solution containing 1% of active substance of the product marketed under the trade name of "Celquat L 200", which is a copolymer of hydroxyethyl cellulose grafted by a radical route with diallyldimethylammonium chloride, were added at ambient temperature and with mechanical stirring to 50 cm$^3$ of an ethanolic solution at an alcohol strength of 20° containing 1% as active substance of the previously neutralized anionic polymer defined in the table.

In Table A below, the measurement of the absolute capillary viscosity of the anionic polymers is carried out in dimethylformamide (DMF) and/or in methanol.

TABLE A

INITIAL MIXTURE

| CARBOXYLIC ANIONIC POLYMER | CATIONIC POLYMER CELQUAT L 200 Proportions | Absolute capillary viscosity Pa s × 10⁻³ (1)10.4 (2)DMF | CH₃OH | Epprecht-Drage viscosity of the thickener formed (3)Pa s |
|---|---|---|---|---|
| Methacrylic acid/methyl methacrylate copolymer | 50/50 | 15 | | 1.550 |
| " | 80/20 | 24.47 | 10.56 | 1.430 |
| Methacrylic acid/methyl acrylate copolymer | 50/50 | | 16.4 | 1.300 |
| " | 80/20 | 17.7 | 8.5 | 1.150 |
| Methacrylic acid/butyl methacrylate copolymer | 85/15 | | 9.94 | 2.000 |
| Methacrylic acid/monoethyl maleate copolymer | 63.6/36.4 | 3.46 | | 0.620 (mod 4) |
| " | 59/41 | 8 | | 1.000 (mod 4) |
| " | 66/34 | 19.2 | | 0.780;1.500 (mod 4) |
| " | 61/39 | 26.8 | | 0.580;1.250 (mod 4) |
| " | 62/38 | 10.4 | | 0.550;1.000 (mod 4) |
| " | 65/35 | 14.1 | | 0.800;1.200 (mod 4) |
| " | 63/37 | 13 | | 1.490;2.000 (mod 4) |
| " | 66/34 | 12 | | 1.700;2.100 (mod 4) |
| " | 68/32 | 19.2 | | 1.700;2.500 (mod 4) |
| " | 72/28 | 14.2 | | 1.380;1.500 (mod 4) |
| Methacrylic acid/N,N—dimethylacrylamide copolymer | 50/50 | | | 0.980 |
| " | 80/20 | 16.3 | | 1.350 |
| Methacrylic acid/diacetoneacrylamide copolymer (4) | 80/20 | | 1.07 | 1.200 |
| Methacrylic acid/N-tert-butylacrylamide copolymer | 80/20 | | 4.06 | 1.050 |
| Methacrylic acid/maleic acid copolymer | 65/35 | 16.7 | | 2.100 |
| " | 70/30 | 13.6 | | 1.800 |
| Methacrylic acid/N—vinylpyrrolidone copolymer | 80/20 | 9.2 | | 1.050 |
| Polymethacrylic acid MW 137,000 | | | 6.8 | 1.400 |
| Polymethacrylic acid MW 186,000 | | | 9.8 | 2.100 |
| Ethylene/maleic anhydride copolymer Monsanto EMA 31 | | 9.82 | 8.15 | 1.600 |

(1)measured at 30° C. in 1% strength solution in water
(2)measured at 30° C. in 5% strength solution in dimethylformamide or methanol
(3)module 3 - measured at 21° C. in 1% strength 10° aqueous alcohol solution - pH = 7.5
(4)viscosity measured using a 1% strength solution of this anionic polymer.

EXAMPLES 2 TO 11

The following gelled compositions for hair styling are prepared (Tables B and C).

When these various compositions are applied to clean wet hair, they impart shape retention to it without leaving a powdery deposit. When they are applied to dried hair it is found that the composition makes styling easier without loading the hair and that, once dried, the latter is soft and has a pleasant feel.

TABLE B

| COMPOSITIONS | EXAMPLE No. 2 | 3 | 4 | 5 | 6 |
|---|---|---|---|---|---|
| Celquat H 100 g % AS | 0.5 | 0.4 | | | |
| Celquat L 200 g % AS | | | 0.8 | 1 | 0.3 |
| Methacrylic acid/monoethyl maleate copolymer (66/34) g % AS | 0.5 | | | | |
| Methacrylic acid/maleic acid copolymer (70/30) g % AS | | 0.6 | | | |
| Methacrylic acid/butyl methacrylate copolymer (85/15) g % AS | | | 0.8 | | |
| Polymethacrylic acid MW 137,000 g % AS | | | | | 0.4 |
| Ethylene/maleic anhydride copolymer Monsanto EMA 31 g % AS | | | | 0.8 | |
| 2-Amino-2-methyl-1-propanol q.s. pH | 8 | 9 | 7 | 6 | 9 |
| Ethyl alcohol q.s. | 20° | | 25° | | 10° |
| Water q.s. g | 100 | 100 | 100 | 100 | 100 |
| Epprecht-Drage viscosity 21° C. 1% in H₂O (module 3) in Pa s | 1.150 | 0.700 | 2.150 | 2.400 | 0.725 |

TABLE C

| COMPOSITIONS | EXAMPLE No. 7 | 8 | 9 | 10 | 11 |
|---|---|---|---|---|---|
| Celquat H 100 g % AS | 0.4 | | | 0.5 | |
| Celquat L 200 | | 1 | 0.66 | | 0.33 |

TABLE C-continued

| COMPOSITIONS | EXAMPLE No. | | | | |
|---|---|---|---|---|---|
| | 7 | 8 | 9 | 10 | 11 |
| g % AS | | | | | |
| Methacrylic acid/N—tert-butylacrylamide copolymer 80/20 g % AS | 0.2 | | | | |
| Methacrylic acid/N,N—dimethyl acrylamide copolymer 80/20 g % AS | | 0.5 | | | |
| Methacrylic acid/methyl methacrylate copolymer 50/50 g % AS | | | 0.33 | | |
| Methacrylic acid/methyl methacrylate copolymer 80/20 g % AS | | | | 1 | |
| Polymethacrylic acid MW 186,000 g % AS | | | | | 0.66 |
| 2-Amino-2-methyl-1-propanol q.s. pH | 8 | 8.5 | 7.5 | 8.5 | 7.5 |
| Ethyl alcohol q.s. | | 30° | 10° | 10° | 10° |
| Perfume, colorant, preservative | | | | | |
| Water q.s. g | 100 | 100 | 100 | 100 | 100 |
| Epprecht-Drage viscosity 21° C. 1% in H$_2$O (module 3) in Pa s | 0.480 | 1.880 | 0.900 | 1.725 | 1.300 |

EXAMPLE 12

An after-shampoo of the following composition is prepared:

| | |
|---|---|
| (A) Celquat L 200 from National Starch | 0.7 g AS |
| (B) 72/28 Methacrylic acid/monoethyl maleate copolymer | 0.7 g AS |
| Distearyldimethylammonium chloride | 1 g |
| Hydrochloric acid q.s. pH: 7 | |
| Water q.s. | 100 g |

This composition is applied to clean, roughly dried hair. After being left in place for a few minutes it is rinsed off with water. The wet hair is smooth and slippery. After drying it is lively and has body.

The gel obtained by interaction of the two polymers A and B has an Epprecht-Drage viscosity at 21° C., module 3, of 1.7 Pa s at a concentration of 1.4% in water.

EXAMPLE 13

An after-shampoo of the following composition is prepared:

| | |
|---|---|
| (A) Celquat L 200 from National Starch | 0.7 g AS |
| (B) 50/50 Methacrylic acid/methyl methacrylate copolymer | 0.7 g AS |
| Quaternized protein sold under the trade name of "Lexein QX 3000" by Inolex | 1 g AS |
| Hydrochloric acid q.s. pH: 6.7 | |
| Water q.s. | 100 g |

This gelled composition is applied to clean, roughly dried hair. After being left in place for a few minutes it is rinsed off with water.

The dried hair is lively and has body.

The gel obtained by interaction of the polymers A and B has an Epprecht-Drage viscosity at 21° C., module 3, of 1.8 Pa s at a concentration of 1.4% in water.

EXAMPLE 14

The following shampoo is prepared:

| | |
|---|---|
| (A) Celquat L 200 from National Starch | 0.5 g AS |
| (B) 50/50 Methacrylic acid/methyl methacrylate copolymer | 0.7 g AS |
| Nonionic surfactant of formula: R—CHOH—CH$_2$O—[CH$_2$—CHOH—CH$_2$O]$_n$-H in which R denotes a mixture of C$_9$-C$_{12}$ alkyl radicals n denotes a statistical mean value of about 3.5 | 10 g AS |
| Hydrochloric acid q.s. pH: 7.4 | |
| Perfume, preservative q.s. | |
| Water | 100 g |

This shampoo has the appearance of a clear gel.

The gel obtained by interaction of the polymers A and B has an Epprecht-Drage viscosity at 21° C., module 3, of 1.65 Pa s at a concentration of 1% in water.

EXAMPLE 15

The following shampoo is prepared:

| | |
|---|---|
| (A) Celquat L 200 from National Starch | 0.7 g AS |
| (B) 72/28 Methacrylic acid/monoethyl maleate copolymer | 0.7 g AS |
| Sodium alkyl ether carboxylate oxyethylenated with 3 moles of ethylene oxide, sold by Marchon under the trade name "Empilan 2747/30" | 10 g AS |
| Hydrochloric acid q.s. pH: 6 | |
| Perfume, preservative q.s. | |
| Water q.s. | 100 g |

This shampoo has the appearance of a clear gel.

The gel obtained by interaction of the polymers A and B has an Epprecht-Drage viscosity at 21°, module 3, of 1.7 Pa s at a concentration of 1.4% in water.

EXAMPLE 16

The following lotion is prepared:

| | |
|---|---|
| (A) Celquat L 200 | 0.1 g |
| (B) Polymethacrylic acid | 0.1 g |
| 2-Amino-2-methyl-1-propanol q.s. pH: 7.5 | |
| Perfume, colorant, preservative q.s. | |
| Water q.s. | 100 g |

This hair-setting lotion is slightly gelled and does not require rinsing.

The gel obtained by interaction of the polymers A and B has an Epprecht-Drage viscosity at 21° C., module 2, of 0.095 Pa s at a concentration of 0.2% in water.

EXAMPLE 17

The following antidandruff composition is prepared:

| (A) Celquat L 200 | 1.5 g |
|---|---|
| (B) 66/34 Methacrylic acid/monoethyl maleate copolymer | 1.2 g |
| 1-Hydroxy-4-methyl-6-(2,4,4-trimethylpentyl)-2(1H)—pyridinone, ethanolamine salt, sold under the trade name "Octopirox" by Hoechst Ethyl alcohol q.s. 30° 2-Amino-2-methyl-1-propanol q.s. pH 7 Preservative, perfume q.s. | 0.1 g |
| Water q.s. | 100 g |

This antidandruff composition has the appearance of a clear gel and it does not require rinsing.

The gel obtained by interaction of the polymers A and B has an Epprecht-Drage viscosity at 21° C., module 3, of about 1.8 Pa s at a concentration of 2.7% in water.

EXAMPLE 18

The following antiseborrhoeic composition is prepared:

| (A) Celquat L 200 | 0.5 g |
|---|---|
| (B) 50/50 Methacrylic acid/methyl methacrylate copolymer | 0.5 g |
| Poly-β-alanine | 1 g |
| 2-Amino-2-methyl-1-propanol q.s. pH 10 Preservative, perfume q.s. | |
| Water q.s. | 100 g |

This antiseborrhoeic composition which can be applied to the skin or to hair has the appearance of a clear gel and does not require rinsing.

The gel obtained by interaction of the polymers A and B has an Epprecht-Drage viscosity at 21° C., module 3, of about 1.2 Pa s at a concentration of 1% in water.

EXAMPLE 19

The support gel for permanent-waving, of the following composition, is prepared:

| Composition 1 | |
|---|---|
| Glycerol monothioglycolate | 68.3 g |
| Glycerin q.s. | 100 g |
| Composition 2 | |
| Celquat L 200 | 1.8 g |
| 70/30 Methacrylic acid/maleic acid copolymer | 1.5 g |
| 2-Amino-2-methyl-1-propanol q.s. pH 6.5 Triethanolamine | 3 g |
| Perfume, colorant, preservative q.s. | |
| Water q.s. | 100 g |

The two compositions 1 and 2 are mixed ad hoc in proportions of 32 g of composition 1 to 87 g of composition 2.

This mixture is applied to hair which is wound onto rollers, for 15 minutes. After 15 minutes in place, it is rinsed off and an oxidizing solution consisting of 8-volume hydrogen peroxide, pH 3, is applied for 10 minutes.

The hair is then rinsed.

EXAMPLE 20

The following direct-dyeing composition is prepared:

| 50/50 Methacrylic acid/methyl methacrylate copolymer | 0.5 g AS |
|---|---|
| Celquat L 200 from National Starch | 0.5 g AS |
| 1-N—(γ-hydroxypropyl)amino-2-nitro-4-N',N'—bis(β-hydroxyethyl)aminobenzene monohydrochloride | 0.1 g |
| 2-Amino-2-methyl-1-propanol q.s. pH 7.5 | |
| Ethyl alcohol q.s. 10° | |
| Preservative q.s. | |
| Water q.s. | 100 g |

This dyeing composition is applied to wet brown hair, washed beforehand. After drying, the hair acquires an ashen brown colour.

EXAMPLE 21

The antipsoriatic composition is prepared by adding 0.5 g of anthraline at the time of use to the gel of the following composition:

| (A) Celquat L 200 | 0.5 g |
|---|---|
| (B) 50/50 Methacrylic acid/methyl methacrylate copolymer | 0.5 g |
| 2-amino-2-methyl-1-propanol q.s. pH 7 | |
| Ethyl alcohol q.s. 10° | |
| Preservative q.s. | |
| Water q.s. | 100 g |

The antipsoriatic composition is applied to the skin and does not require rinsing.

The gel obtained by interaction of the polymers A and B has an Epprecht-Drage viscosity at 21° C., module 3, of about 1.2 Pa s at a concentration of 1% in water.

EXAMPLE 22

The following antiacne composition is prepared by adding 5 g of benzoyl peroxide at the time of use to the gel whose composition is given in Example 21.

This composition is applied to the skin.

EXAMPLE 23

The following bactericidal composition is prepared by adding 1 g of 5-chloro-2-(2,4-dichlorophenoxy)-phenol or triclosan (DCI) sold under the name of "Irgasan DP 300" at the time of use to the gel whose composition is given in Example 21.

This composition is applied to the skin.

EXAMPLE 24

A hair-conditioning composition is prepared by adding 18 g of iris powder diluted with 36 g of water to 46 g of a gel of the following composition:

| (A) Celquat L 200 | 4.5 g |
|---|---|
| (B) 80/20 Methacrylic acid/N—vinylpyrrolidone copolymer | 4.5 g |
| Ethyl alcohol q.s. 10° | |
| 2-Amino-2-methyl-propanol q.s. pH 7.5 | |
| Perfume, preservative q.s. | |

| -continued | |
|---|---|
| Water q.s. | 100 g |

The composition is applied to washed hair. After rinsing, the hair has a soft feel.

The gel obtained by interaction of the polymers A and B has an Epprecht-Drage viscosity at 21° C., module 4, of 11.7 Pa s at a concentration of 9% in water.

EXAMPLE 25

The following restructuring rinsing lotion is prepared by adding 1.5 g of dimethylolethylenethiourea at the time of use to the gel of Example 21 at pH 6.

This composition is applied to damaged hair.

We claim:

1. Thickening agent resulting from the ionic interaction of a cationic polymer consisting of a copolymer of cellulose or of a cellulose derivative which is grafted with a quaternary ammonium salt of a water-soluble monomer, said cationic polymer having an absolute capillary viscosity at 1% in water at 30° C. which is less than 0.025 Pa s, and of a carboxylic anionic polymer having a molecular weight of 500 to 3,000,000, said carboxylic anionic polymer having an absolute capillary viscosity at a concentration of 5% in dimethylformamide or methanol at 30° C. which is less than or equal to 0.030 Pa s, said thickening agent having an Epprecht-Drage viscosity, module 3, higher than or equal to 0.45 Pa s in solution at a concentration of 1% in water at 21° C., and the weight ratio of said cationic polymer to said carboxylic anionic polymer in said thickening agent being in the range of 1/5 to 5/1.

2. Thickening agent according to claim 1, wherein the cationic polymer is chosen from hydroxyalkyl cellulose copolymers grafted by a radical route with a quaternary ammonium salt of a water-soluble monomer chosen from methacryloylethyltrimethylammonium, methacrylamidopropyltrimethylammonium and dimethyldiallylammonium salts.

3. Thickening agent according to claim 1 wherein the carboxylic anionic polymer is chosen from methacrylic acid homopolymers having a molecular weight greater than 20,000, as determined by light scattering, and copolymers of methacrylic acid with a following monomer: a $C_1$-$C_4$ alkyl acrylate or methacrylate, an acrylamide derivative, maleic acid, a $C_1$-$C_4$ monoalkyl maleate, N-vinylpyrrolidone and copolymers of ethylene with maleic anhydride.

4. Thickening agent according to claim 1, wherein the anionic polymer is chosen from copolymers of methacrylic acid with methyl methacrylate whose absolute capillary viscosity measured in solution in dimethylformamide at a concentration of 5% and at 30° C. is of the order of 0.015 Pa s, a copolymer of methacrylic acid with monoethyl maleate having an absolute capillary viscosity, measured in solution in dimethylformamide at a concentration of 5% and at 30° C., of the order of 0.013 Pa s, a copolymer of methacrylic acid with butyl methacrylate whose absolute capillary viscosity, measured in solution in methanol at a concentration of 5% and at 30° C., is of the order of 0.010 Pa s, and a copolymer of methacrylic acid with maleic acid whose absolute capillary viscosity, measured in solution in dimethylformamide at a concentration of 5% and at 30° C., is of the order of 0.016 Pa s.

5. Thickening agent according to claim 1, resulting from the ionic interaction in an aqueous medium containing 0.01 to 6% of said cationic polymer and 0.01 to 6% of said carboxylic anionic polymer.

6. Cosmetic composition intended for the treatment of hair, of the skin and of the nails, containing a thickening agent as defined in claim 1.

7. Cosmetic composition according to claim 6, wherein the thickening agent is present in proportions of between 0.02 and 12% by weight based on the total weight of the composition.

8. Composition according to claim 6, having a pH of between 6 and 12.

9. Composition according to claim 6, intended to be employed as a thickened or gelled lotion for hair-setting or for blow-drying, containing additionally nonionic polymers chosen from polyvinylpyrrolidones, copolymers of polyvinylpyrrolidone with vinyl acetate, or anionic polymers chosen from copolymers of vinyl acetate with an unsaturated carboxylic acid, the copolymers resulting from the polymerization of vinyl acetate with crotonic acid and an acrylic or methacrylic ester, the copolymers resulting from the copolymerization of vinyl acetate with a vinyl alkyl ether and an unsaturated carboxylic acid, the copolymers resulting from the copolymerization of vinyl acetate with crotonic acid and a vinyl ester of an acid containing a long carbon chain or an allyl or methallyl ester of an acid containing a long carbon chain.

10. Cosmetic composition according to claim 6, to be used as a shampoo containing one or more surface-active agents with a detergent property which are chosen from anionic, cationic, nonionic or amphoteric surfactants or mixtures thereof.

11. Cosmetic composition according to claim 6, intended to be rinsed off, containing conditioning agents chosen from quaternary proteins, cationic silicone polymers, cationic surfactants and cationic polymers other than polymers of cellulose or of cellulose derivatives grafted by a radical route with a quaternary ammonium water-soluble monomer.

12. Cosmetic composition intended to be employed for hair-setting, containing in an aqueous or aqueous-alcoholic medium, a thickener resulting from the ionic interaction of 0.1 to 1.5% by weight of a hydroxyethyl cellulose copolymer grafted by a radical route with diallyldimethylammonium chloride having an absolute capillary viscosity at 1% in water at 30° C. which is less than 0.025 Pa s and of 0.1 to 1.5% by weight of a copolymer of methacrylic acid with methyl methacrylate or with monoethyl maleate or with butyl methacrylate whose absolute capillary viscosity, measured at 30° C. in solution in dimethylformamide or methanol at a concentration of 5%, is between 0.010 and 0.015 Pa s, the copolymer of methacrylic acid having a molecular weight of 500 to 3,000,000, the Epprecht-Drage viscosity of the thickener, measured at 21° C., module 3, diluted to a concentration of 1% in water, being higher than 0.450 Pa s, the pH of the composition being between 6.5 and 9, and the thickener being present in the composition in an amount of 0.02 to 12% by weight, based on the total weight of the composition.

13. Process for thickening or gelling aqueous cosmetic compositions, comprising the introduction of at least one thickener as defined in claim 1 into these compositions so as to give an Epprecht-Drage viscosity measured at 21° C. (module 3) which is equal to or higher than 0.450 Pa s at a concentration of 1% in water.

14. Process for the treatment of hair, of the skin or of the nails, wherein at least one cosmetic composition as defined in claim 6 is applied to said tissues.

15. Process for the treatment of hair, of the skin or of the nails, wherein the composition defined in claim 9 is applied to the said tissues, this application not being followed by a rinse.

* * * * *